United States Patent [19]

Hollingsworth et al.

[11] Patent Number: 5,262,562

[45] Date of Patent: Nov. 16, 1993

[54] POLYETHER GLYCOL PRODUCTION BY POLYMERIZATION OF TETRAHYDROFURAN

[75] Inventors: Donald R. Hollingsworth; John F. Knifton, both of Austin, Tex.

[73] Assignee: Texaco Chemical Company, White Plains, N.Y.

[21] Appl. No.: 835,876

[22] Filed: Feb. 14, 1992

[51] Int. Cl.$^5$ ............................................. C07C 67/24
[52] U.S. Cl. ............................................................ 560/240
[58] Field of Search ............................................ 560/240

[56] References Cited

U.S. PATENT DOCUMENTS

| | | | |
|---|---|---|---|
| 4,243,799 | 1/1981 | Mueller et al. | 560/240 |
| 4,605,806 | 8/1986 | Ballantine | 568/678 |
| 4,803,299 | 2/1989 | Mueller | 568/617 |

Primary Examiner—José G. Dees
Assistant Examiner—Joseph M. Conrad, III
Attorney, Agent, or Firm—James L. Bailey; Kenneth R. Priem; Cynthia L. Kendrick

[57] ABSTRACT

A method is disclosed wherein tetrahydrofuran is reacted in the presence of acetic anhydride and a catalyst to provide acetate derivatives of polyglycols and using as a catalyst a triflic acid-modified montmorillonite clay at a temperature of 0°–1000° C. and atmospheric pressure.

14 Claims, 1 Drawing Sheet

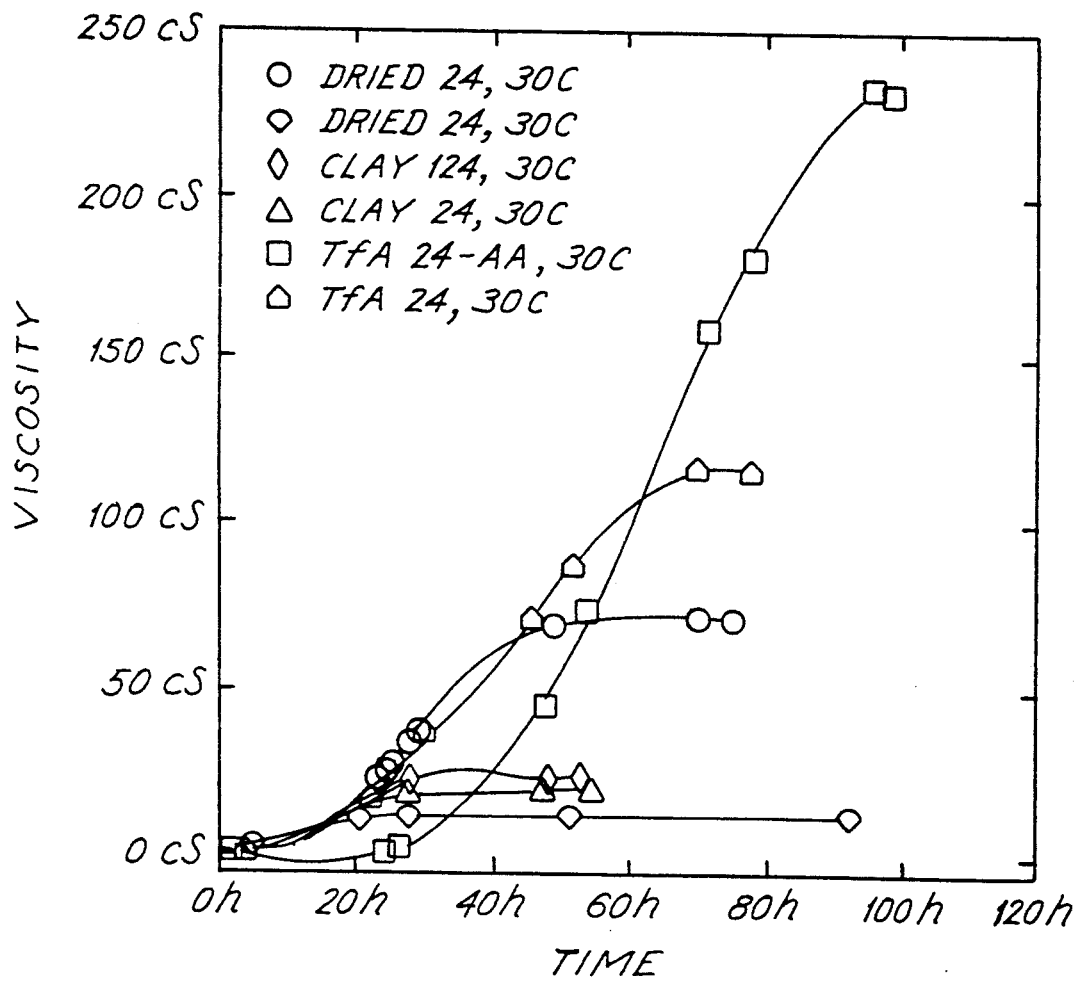

POLYETHER GLYCOL PRODUCTION BY POLYMERIZATION OF TETRAHYDROFURAN

FIELD OF THE INVENTION

This invention concerns a method for preparation of polyether glycols. More particularly it concerns an improved method for preparation of polyether glycols and their acetate derivatives which comprises polymerization of tetrahydrofuran in the presence of a fluorosulfonic acid-modified montmorillonite clay catalyst and an acetic anhydride coreactant. The method demonstrates improved rates of tetrahydrofuran polymerization and increased viscosity of the polyether glycol derivative products. Conversion is as high as >70% and viscosity is as high as 23 cS.

BACKGROUND OF THE INVENTION

The ring-opening polymerization of tetrahydrofuran was reported in 1937 by Meerwein, using a trialkyloxonium salt as a catalyst. A review by Meerwein of the polymerization of tetrahydrofuran is found in *Angew. Chem.* 72, 927 (1960).

In subsequent years a number of other researchers have contributed to knowledge of tetrahydrofuran polymerization catalysts and mechanisms.

Generally, initiation requires the formation, in some manner, of a THF oxonium ion. The species R

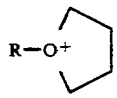

must be formed in order for the propagation reaction to take place. The different ways in which this species can be formed are conveniently grouped as follows:

1. Reaction with preformed trialkyl oxonium salts.
2. In situ formation of oxonium ion.
3. Addition of a carbonium ion.
4. Hydrogen abstraction (Adv. Poly. Sci., 4, 528 (1967). page 537.)

Ibid at page 531, there is a discussion of catalysts for tetrahydrofuran polymerization. These include combinations of metal halides, unsaturated tertiary oxonium salts, complex inorganic acids, catalysts of Lewis acid class, such a $PF_5$, alkyl ammonium compounds used with water or epichlorohydrin, and certain related complex ions. At page 536 there is a discussion of the "Mechanism of Polymerization."

In an article by M. P. Dreyfuss et al., titled "The Reaction of Trityl Salts with 2-Methyltetrahydrofuran and with Tetrahydrofuran", in *Macromolecules*, 1, 437 (1968), there is a discussion of the use of trityl salts as initiators in the preparation of cyclic ethers. Trityl salts include, for example, $Ph_3CClO_4$ and $Ph_3CPF_6$. One disadvantage of using these salts to polymerize tetrahydrofuran, as noted at page 440, is that the products are characteristically dark colored.

Oxonium ions have been studied as initiators. These ions are discussed in an article titled "The Mechanism of the Initiation Reaction of the Cationic Polymerization of Tetrahydrofuran by Stable Cationic Salts", by Y. Yamashita, et al., in *Die Makromolekulare Chemie*, 142, 171-181 (1971). At page 172 it is noted that triethyloxonium salts were shown to initiate the polymerization of tetrahydrofuran by the straight forward alkyl exchange reaction. In the examples of this reference it is noted on page 175 that the reactivity of the cyclic ethers could be correlated with basicity.

Metal salts as initiators are discussed in "Use of Mono-and Multifunctional Oxocarbenium Salts in the Polymerization of Tetrahydrofuran", by E. Franta, et al., *J. Polymer Sci.*: Symposium No. 56, 139-148 (1976). In this work oxocarbonium salts were found useful as initiators for the polymerization of tetrahydrofuran and allowed the polymerization to proceed without termination. Mono- and difunctional initiators were prepared which reacted rapidly and were used to prepare block copolymers and graft copolymers of controlled structure.

In a book titled "Polymerization of Aldehydes and oxides", J. Furukawa et al., Interscience Publishers, 1963, Chapter V is a review titled "Polymerizations of Tetrahydrofuran and 1,4-Epoxycyclohexane." It is noted at page 225 that the polymer of tetrahydrofuran is a mobile liquid and a viscous liquid, or a solid, depending on its molecular weight. The softening point of the solid polymer is so low (41°±20° C.) that it has no practical applications without any processing. This reference provides a review of the various classifications of trialkyloxonium salt catalysts used in the polymerization of tetrahydrofuran. A model is projected for the polymerization of a substituted tetrahydrofuran wherein the melting points and other properties could be manipulated.

U.S. Pat. No. 2,856,370, to Muetterties, discloses a polytetrahydrofuran prepared with a phosphorous pentafluoride catalyst, having a melting point above 100° C.

E. P. 428,003 A2 discloses the use of heteropolyacid catalysts in polymerization of tetrahydrofuran.

P. Dreyfuss has authored a reference titled "Poly(tetrahydrofuran)", Gordon and Breach Science Publishers, 1982. Chapter seven contains a discussion of the industrial applications of polytetrahydrofuran in polyurethane and polyester thermoplastic elastomers. At page 194 it is stated that commercial polyurethanes and polyesters containing polytetrahydrofuran are usually based on $\alpha,\omega$-difunctional precursors of relatively low molecular weight which are most often diprimary diols. An example is poly(tetramethylene ether) glycol(PTMEG).

At page 196, Ibid, there is a discussion of methods of initiating polymerization of tetrahydrofuran with fluorosulfonic acid to yield PTHF in which it is possible to have hydroxyl groups at both ends after treatment with water. A noted disadvantage is that acids used for initiation cannot be recovered for further use and disposal of the acidic by-products is a problem, due to their toxicity and corrosiveness. Strong acids can cause the degradation of the PTMEG. In addition, the presence of hydroxyl groups during polymerization markedly increases molecular weight and broadens the molecular weight distribution. Some of these disadvantages can be overcome by polymerization of tetrahydrofuran using a strong protonic acid in the presence of acetic anhydride. It is mentioned at page 197 that Nafion resin ($NfSO_3H$) may be used as a strong-acid catalyst and that when PTHF glycols are prepared using this resin, the reaction mixture normally contains acetic anhydride and acetic acid in addition to tetrahydrofuran. Data indicates that the ratio of anhydride to acid serves as a means of controlling the molecular weight of resulting PTHF diacetates. At page 200, there is disclosed the use of an anhydride of a very strong acid as an initiator to form PTHF having oxonium ions on both ends of the chain which can be treated with water to form PTMEG. The use of Polymer Polyols for High Performance urethane elastomers is discussed at page 197. No. 10131/8.

The use of clays as catalysts for selected applications is known in the art. In an article titled "Catalysis: Selective Developments", Chem. Systems Report 84-3, 239-249, at section 3.4320, the unusual properties of smectite clays which make them of interest as catalysts are discussed. These compositions are layered and exhibit a 2:1 relationship between tetrahedral and octahedral sites. In addition the combination of cation exchange, intercalation and the fact that the distance between the layers can be adjusted provide interesting possibilities.

There is a discussion of clay mineral catalysts, including "acid" montmorillonite clay catalysts in "Progress in Inorganic Chemistry", Vol. 35, p. 41 (1987). The process of pillaring this type of catalyst is discussed. Pillaring can convert a clay lamellar solid into a more heat resistant two dimensional zeolite material.

G. B. Patent No. 2,179,563 (1987) discloses the use of modified layered clay catalysts in reactions capable of catalysis by protons. Of particular interest in this invention were the three-layer sheet types, such as smectites, micas and vermiculites composed of successive layers of tetrahedral silica, octahedral alumina and tetrahedral silica which can exhibit swelling properties.

U.S. Pat. No. 4,590,294 discloses a process for the production of an ester comprising reacting an olefin from the group consisting of ethylene, hex-1-ene, hept-1-ene, oct-1-ene, 4-methylpent-1-ene, hex-2-ene, 1,5-hexadiene and cyclohexene with a carboxylic acid using as a catalyst component a hydrogen ion-exchanged layered clay.

Copending U.S. patent application Ser. No. 07/494,280 discloses the reaction of butanol and methanol in the presence of acidic montmorillonite clay catalysts having certain identifiable physical parameters, such as surface area, acidity range and moisture content.

In U.S. Pat. No. 4,189,566 there is disclosed a process for the preparation of polybutylene glycol carboxylic acid esters by polymerizing tetrahydrofuran, wherein the tetrahydrofuran, after removal of the catalyst used for preparation of tetrahydrofuran, is treated before polymerization with a strong mineral acid, an organic sulfonic acid, silica gel and/or a bleaching earth and is then polymerized in the presence of one or more carboxylic acids and/or carboxylic acid anhydrides and a polymerization catalyst.

U.S. Pat. No. 4,243,799 discloses an improvement of U.S. Pat. No. 4,189,566 wherein a bleaching earth is used which contains less than 3% by weight of water, said catalyst being arranged in a fixed bed and passing a mixture of pretreated tetrahydrofuran and carboxylic anhydride through said fixed bed.

The object of this improvement is to decrease the amount of discoloration and to affect the selectivity for certain molecular weights.

None of the cited references suggest the use of montmorillonite clay catalysts in the polymerization of cyclic ethers, and especially not tetrahydrofuran.

From the references reviewed above it would appear that methods of polymerizing tetrahydrofuran are of great interest in the art. It is also noted from the description of relevant research that there have been attempts to produce polymerization products having greater viscosity and to find catalysts which enhance conversion, yet exhibit fewer disadvantages. In addition, improvements in rate of conversion are always desirable commercially.

It would be a distinct advance in the art if a catalyst were available which allowed for an improved rate of polymerization of tetrahydrofuran, improved viscosity and improved conversion while producing fewer acid by-products with their inherent disadvantages. These properties would also make the products more useful in injection molding techniques, see "Poly(tetrahydrofuran)", supra, p. 238.

It has now been discovered that the use of a triflic acid-modified montmorillonite clay in the polymerization of tetrahydrofuran results in an improved rate of conversion and in increased viscosity of the liquid polyether glycol products.

SUMMARY OF THE INVENTION

In accordance with certain of its aspects, the novel method of this invention for preparing polyether glycols as acetate derivatives comprises polymerization of tetrahydrofuran in the presence of a fluorosulfonic acid-modified montmorillonite clay catalyst and an acetic anhydride coreactant.

BRIEF DESCRIPTION OF THE DRAWING

FIG. 1 represents a comparison of time versus viscosity for specified catalysts.

DETAILED DESCRIPTION OF THE INVENTION

In this invention polyether glycols are produced, particularly as their acetate derivatives by polymerizing tetrahydrofuran, using acetic anhydride as a coreactant. The catalyst is a montmorillonite clay modified with a fluorosulfonic acid.

The reaction can be best represented by the following:

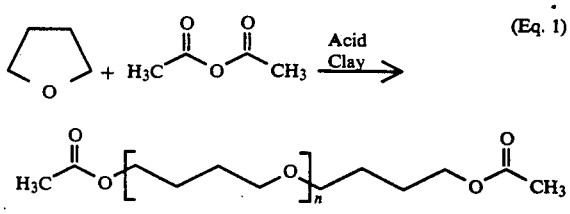

(Eq. 1)

Generally the polytetrahydrofuran and acetic anhydride coreactant may be mixed in greatly varying proportions in order to generate the desired polyether glycols, but preferably the molar ratio of polytetrahydrofuran to acetic anhydride should be between 10:1 and 1:10, in order to achieve the improved yields of polyether glycol. In order to achieve maximum selectivity to polyether glycol and optimum conversion per pass, an excess of tetrahydrofuran in the liquid feed is desirable. The most preferred polytetrahydrofuran to acetic anhydride molar ratio is from 1:5 to 1:1.

Good results were realized using certain fluorosulfonic acid (triflic acid) modified clays as catalysts for the reaction in Eq. 1, particularly the trifluoromethanesulfonic acid (triflic acid) modified montmorillonite clays.

The clays used to form this catalyst are silica-alumina clays. Chemically, clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

Particularly effective in the reaction (Eq. 1) are smectite clays. Smectite clays are discussed in the article cited in Chem. Systems Report, 84-3. These clays have small particle size and unusual intercalation properties which afford them high surface area. They are alumino silicates with a unique structure that permits modifications which provide useful catalysts. They comprise layered sheets of octahedral sites between sheets of tetrahedral sites, where the distance between the layers can be adjusted by swelling. This layering is illustrated in an article by F. Figueras, Catal. Rev.-Sci. Eng., 30, 457 (1988). What renders the smectites of interest among the clay minerals is the combination of cation exchange, intercalation, and the fact that the distance between the layers can be adjusted by treatment with the appropriate solvent etc.

The three layered sheet types include montmorillonite, vermiculite and some brittle mica. The idealized basic structure of clays of this type is that of a pyrophyllite which has the basic formula $Si_8Al_4O_{20}(OH)_4$.

A general representation of the montmorillonite structure is:

$$M_{x/n}{}^{n+} \cdot yH_2O(Al_{4-x}Mg_x)(Si_8)O_{20}(OH)_4$$

Where: M represents the interlamellar (balancing cations), normally sodium or lithium and x, y and n are integers.

Said montmorillonite clays are best treated with fluorosulfonic acids as demonstrated in Example 1 or they can be pretreated with a mineral acid before the fluorosulfonic acid is added, as in Example 2. Mineral acids such as sulfuric acid and phosphoric acid activate montmorillonites by attacking and solubilizing structural cations in the octahedral layers. This opens up the clay structure and increases surface area. These acid-treated clays act as strong Bronsted acids.

It has been discovered that fluorosulfonic anhydride- or acid-modified clays (triclays) possess a number of properties for the improved polymerization of tetrahydrofuran. The acid or anhydride useful for modifying the montmorillonite clay is selected from the group consisting of fluorosulfonic acid and its congeners. These fluorosulfonic acids or anhydrides can be substituted with an alkyl group as in the case of trifluoromethanesulfonic acid (triflic acid) or trifluoromethanesulfonic anhydride.

Where the montmorillonite clays are treated with a mineral acid, said clays should preferably have a residual acidity in the range 0.1 to 30 mg KOH/gm (titrated to phenolphthalein end point), a surface area of 10 to 1000 m²/gm, and a moisture content of up to 20 wt%. Illustrative examples include Engelhard Powdered Clay-124, having a residual acidity of 14 mg KOH/gm, surface area of 350 m²/gm and a moisture content of 4 wt%, granular Clay-24, of particle size 20/60 mesh, having an acidity of 16 mg KOH/gm, a surface area of 300 m²/gm and a moisture content of 10 wt%, granular Clay-25, of particle size 10/20 mesh, having an acidity of 16 mg KOH/gm, a surface area of 400 m²/gm and a moisture content of 12 wt%, as well as dried Clay-24.

Most preferred are montmorillonite clays with a residual titratable acidity in the range of 1 to 20 mg KOH, a surface area of 100 to 500 m²/gm and a moisture content of <10%. Illustrative of such clays is Engelhard's Grade-124 clay in granular form.

The performance of all fluorosulfonic acid-modified clays in polyether glycol synthesis from tetrahydrofuran and acetic anhydride in one-step (Eq. 1) is illustrated by the accompanying examples.

Said catalysts may be in the form of powders, pellets, granules, spheres, shapes and extrudates. The examples described herein demonstrate certain advantages using granules.

The reaction may be carried out in either a stirred slurry reactor or in a fixed bed continuous flow reactor. The catalyst concentration should be sufficient to provide the desired catalytic effect.

Polymerization can generally be conducted at temperatures from 0° to 100° C.; the preferred range is 30° to 70° C. The total operating pressure may be from 1 atm to 100 atm, or higher. The preferred pressure range is close to atmospheric.

Conversions of tetrahydrofuran in wt% are estimated in the following examples using the equation:

$$\frac{(\text{Wt \% Conc. of THF in Feed} - \text{Wt \% Conc. of THF in Product})}{\text{Wt \% Conc. of THF in Feed}} \times 100$$

Selectivities of polyether glycols are estimated from:

$$\frac{\text{Moles of Polyether Glycols in Product}}{\text{moles of THF converted}} \times 100$$

The equilibrium point of the reaction in the instant method was measured by monitoring the changes in viscosity over time. It should be noted that measured viscosity depends in this case on the extent of conversion as well as average degree of polymerization. In other words, as a few tetrahydrofuran molecules begin to polymerize, the resultant oligomers will begin to influence the overall viscosity of the mixture. But lower molecular weight oligomers will affect viscosity only after a reasonable conversion has been achieved. Therefore, it is conceivable to have two very different mixtures that give approximately the same viscosity measurements (i.e. high conversion and low molecular weight polymers or low conversion and high molecular weight polymers).

This knowledge regarding viscosity was used in devising a way to evaluate the relative catalyst effectiveness. As a baseline, tetrahydrofuran was stirred in the presence of the Clay 124 or dried Clay 24 (heated in vacuo at 200° C. for 7 hours) at 30° (Examples 9 and 10). A kinematic viscosity measurement was periodically taken, however, no increase in viscosity was observed after 7 hours. It was found that when tetrahydrofuran and acetic anhydride were stirred at 30° C. in the presence of Clay 124, the viscosity increased gradually for 53 hours reaching a maximum viscosity of 23 centistoke(cs) (Example 11).

At this point, the viscosity began to decrease and the reaction was stopped, giving an average molecular weight material of 683 and a conversion of 61%. The same procedure was applied using dried Clay 24, triflic acid treated Clay 24 and untreated Clay 24 (Examples 12-14).

FIG. 1 is a graph comparing the results where time is plotted against viscosity. In the legend of this figure TfA 24 is used to represent triflic acid treated Clay 24. In the first attempt, TfA 24-AA, using triflic acid-treated Clay 24 and delayed (24 hour) addition of acetic anhydride, at 30° C., acetic anhydride was added only because the viscosity had not increased after 24 hours, thus demonstrating that even this clay needs an activator to perform optimally. However, once added, this catalyst significantly outperformed the other catalysts. When the run was repeated, adding acetic anhydride only at the beginning, the increase in performance was not so dramatic. Thus, a delayed addition phenomena of one to 48 hours seems to be advantageous for this catalyst.

Example A illustrates a typical preparation of a trifluoromethane sulfonic acid(triflic acid)-modified montmorillonite clay catalyst.

Example B illustrates a typical preparation of a triflic acid-modified clay that had previously been acidified with sulfuric acid.

Table I and FIG. 1 illustrate the preparation of homopolymers of THF using as a catalyst:

a) Triflic acid-modified montmorillonite clays (triclays).
b) Sulfuric acid-modified montmorillonite clays (Clay 24 and Clay 124).
c) Boron trifluoride catalysts of the prior art.

EXAMPLE A

This example illustrates the preparation of a trifluoromethanesulfonic acid-modified clay.

To 85 g of a neutral montmorillonite clay (Engelhard Grade 2C Powder, dried at 175° C. in vacuo) was added a solution of trifluoromethanesulfonic acid (10.0 g) in dried acetone (100cc). The mixture was stirred for 24 hours under a nitrogen blanket, filtered and the solids washed first with acetone and water, then dried in vacuo at 40° C. overnight and at 150° C. for 4 hours.

The recovered pale yellow powder was found to contain by analysis:
$H_2O = 0.73\%$
Acidity = 0.19 meq/g

EXAMPLE B

This example illustrates the preparation of another trifluoromethane sulfonic acid-modified clay.

To 100 g of a montmorillonite clay that had been previously treated with sulfuric acid (Engelhard Grade 124, granules, titratable acidity 7.0 mg KOH/g) was added a solution of trifluoromethanesulfonic acid (5.0 g) in dried acetone (150 cc). The mixture was stirred for 3-4 hours under an inert atmosphere, filtered and the solids washed with acetone and water, then dried in vacuo at 40° C. overnight, plus 150° C. for 5 hours.

EXAMPLES 1-21

These examples illustrate the production of polyether glycols via the polymerization of tetrahydrofuran in the presence of various acid-modified montmorillonite clay catalysts, including triflic acid-modified montmorillonite clays.

Examples 19-21 show the comparative performance of boron trifluoride or boron trifluoride etherate of the prior art.

PROCEDURE FOR THE EXAMPLES OF TABLE 1

The catalyst was added to a flask equipped with a mechanical stirrer, thermometer, condenser and nitrogen inlet. To this was added THF (dried over 4A molecular sieves) followed by acetic anhydride. The mixture was heated to the desired temperature and the viscosity was monitored throughout the reaction. After the desired reaction time was reached or no viscosity increase was observed, the unreacted THF and acetic anhydride were removed under reduced pressure. The residue was weighted and analyzed.

The desired polyether glycol liquid products of MW Ca. 300-1200 were prepared in Examples 1-18 using various triflic acid or sulfuric acid-modified clays. By comparison, the boron trifluoride catalysts of the prior art give undesirable high MW gels under similar conditions (Examples 19-21).

FIG. 1 illustrates the improved viscosity and product performance of liquid polyether glycol products made using the triflic acid-modified clay. The conversion reaches 71% in this case (Example 14).

TABLE I

| Ex. | THF grams | Anhydride grams | mol % | Catalyst Used | Catalyst grams | Catalyst wt % | Temp °C. | Time Hours | Recovered grams | Conversion % | SAP # meq/g | MW by SAP# | MW by GPC | Acidity mg KOH/g | Water wt % |
|---|---|---|---|---|---|---|---|---|---|---|---|---|---|---|---|
| 1 | 500 | 83 | 12 | Clay 124 | 25 | 4.3 | 30 | 7.5 | 134 | 23 | 1.99 | 1005 | 764 | | |
| 2 | 500 | 50 | 7 | Clay 124 | 25 | 4.3 | 30 | 7 | 138 | 25 | 1.85 | 856 | 604 | 0.97 | |
| 3 | 500 | 83 | 12 | Clay 124 | 25 | 4.3 | 30 | 7.5 | 135 | 23 | 2.21 | 629 | | 0.33 | 0.03 |
| 4 | 500 | 83 | 12 | Clay 124 | 25 | 4.3 | 30 | 48 | 401 | 69 | 3.24 | 642 | 562 | 6.87 | |
| 5 | 500 | 83 | 12 | Clay 124 | 11.7 | 2.0 | 35 | 8 | 103 | 18 | 1.96 | 1020 | | | |
| 6 | 500 | 83 | 12 | Clay 124 | 11.7 | 2.0 | 50 | 7 | 145 | 25 | 3.54 | 565 | 296 | | 0.121 |
| 7 | 500 | 80 | 11 | Clay 124 | 25 | 4.3 | 50 | 6 | 258 | 44 | 3.27 | 629 | | 0.33 | |
| 8 | 500 | | 12 | Clay 124 | 11.7 | 2.0 | 70 | 7 | 251 | 43 | 5.38 | 372 | | | |
| 9 | 500 | | 0 | Clay 124 | 25 | 5.0 | 30 | 7 | 2 | 0 | | | | | |
| 10 | 500 | | 0 | dried 24 | 25 | 5.0 | 50 | 7 | 0 | 0 | | | | | 0.029 |
| 11 | 504 | 71.4 | 10 | Clay 124 | 25.2 | 4.4 | 30 | 53 | 281 | 61 | 2.93 | 683 | | 4.02 | 0.148 |
| 12 | 504 | 71.4 | 10 | dried 24 | 25.2 | 4.4 | 30 | 77.5 | | 42 | 2.98 | 671 | | 1.74 | 0.016 |
| 13 | 504 | 71.4 | 10 | Clay 24 | 25.2 | 4.4 | 30 | 54 | 268.5 | 57 | 2.76 | 725 | | 3.61 | 0.024 |
| 14 | 504 | 71.4 | 10 | TriClay 24 | 25.2 | 4.4 | 30 | 73 | 304.7 | 71 | 2.62 | 763 | | 1.64 | 0.043 |
| 15 | 504 | 71.4 | 10 | dried 24 | 25.2 | 4.4 | 50 | 92 | | 51 | 3.61 | 554 | 830 | 1.22 | 0.092 |
| 16 | 504 | 71.4 | 10 | TriClay 24 | 25.2 | 4.4 | 30 | 142 | | | 2.78 | 719 | | | |
| 17 | 500 | 83 | 12 | Clay 24 | 25 | 4.3 | 30 | 7 | 150 | 26 | 2.28 | 758 | | 1.86 | 0.016 |
| 18 | 504 | 71.4 | 10 | dried 24 | 25.2 | 4.4 | 30 | 7 | 181.4 | 32 | 2.03 | 985 | | 0.73 | |
| 19 | 500 | | 0 | BF$_3$Et$_2$O | 5 | 1.0 | 30 | 24 | 0 | 0 | | | | | |
| 20 | 410 | | 0 | BF$_3$Et$_2$O | 81 | 19.8 | 30 | 2.5 | 131 | 32 | | | | | |

TABLE I-continued

| Ex. | THF grams | Anhydride grams | mol % | Catalyst Used | Catalyst grams | Catalyst wt % | Temp °C. | Time Hours | Recovered grams | Conversion % | SAP # meq/g | MW by SAP# | MW by GPC | Acidity mg KOH/g | Water wt % |
|---|---|---|---|---|---|---|---|---|---|---|---|---|---|---|---|
| 21 | 504 | | 0 | BF$_3$ | 47.5 | 9.4 | 35 | 7 | 9 | 2 | | 59002* 26855* | | | |

*59002 by intrinsic viscosity
*26855 by intrinsic viscosity

We claim:

1. In a method wherein tetrahydrofuran is reacted with acetic anhydride in the presence of a catalyst to provide polyether glycols, an improvement providing higher rates of polymerization and polyether glycols having increased viscosity which comprises reacting tetrahydrofuran at mild temperature and pressure conditions in the presence of a catalyst comprising montmorillonite clay having a water content of from 4 wt% to 20 wt%, modified with a fluorosulfonic acid, fluorosulfonic acid anhydride, trifluoromethanesulfonic acid or trifluoromethanesulfonic acid anhydride, and adding the acetic anhydride is after between 1 and 48 hours.

2. The method of clay 1 wherein the fluorosulfonic acid is trifluoromethanesulfonic acid.

3. The method of claim 1 wherein the fluorosulfonic anhydride is trifluoromethanesulfonic anhydride.

4. The method of claim 1 wherein the montmorillonite clay catalyst is pretreated with a mineral acid before the fluorosulfonic acid is deposited thereon.

5. The method of claim 4 wherein the mineral acid is selected from the group consisting of phosphoric acid and sulfuric acid.

6. The method of claim 1 wherein said montmorillonite clay has the structure:

$$M_{x/n}{}^{n+} \cdot yH_2O(Al_{4-x}Mg_x) Si_8) O_{20}(OH)_4$$

Where:
M represents the interlamellar balancing cations, normally sodium or lithium and x, y and n are integers.

7. The method of claim 4 wherein the sulfuric acid or phosphoric acid-treated clay has a residual acidity in the range 0.1 to 30 mg KOH/gm.

8. The method of claim 6 wherein the clay has a surface area of 10 to 1000 m$^2$/gm.

9. The method of claim 6 wherein the clay has a residual acidity of 14 mg KOH/gm, surface area of 350 m$^2$/gm and a moisture content of 4 wt%.

10. The method of claim 6 wherein the clay has a residual acidity of 16 mg KOH/gm, a surface area of 300 m$^2$/gm and a moisture content of 10 wt%.

11. The method of claim 6 wherein the clay has an acidity of 16 mg KOH/gm, a surface area of 400 m$^2$/gm and a moisture content of 12 wt%.

12. The method of claim 1 wherein the temperature is from about 0° C. to 100° C.

13. The method of claim 1 wherein the pressure is from about 1 atm to 100 atm.

14. The method of claim 1 wherein the temperature is from about 30° C. to 70° C.

* * * * *

UNITED STATES PATENT AND TRADEMARK OFFICE
CERTIFICATE OF CORRECTION

PATENT NO. : 5,262,562
DATED : November 16, 1993
INVENTOR(S) : Donald Ray Hollingsworth
John Frederick Knifton It is certified that error appears in the above-indentified patent and that said Letters Patent is hereby corrected as shown below:

Claim 2, Col. 9, line 27, please delete "clay" and insert therefor --Claim--.

Signed and Sealed this

Nineteenth Day of April, 1994

Attest:

BRUCE LEHMAN

Attesting Officer     Commissioner of Patents and Trademarks